(12) United States Patent
Ishibashi

(10) Patent No.: US 7,558,620 B2
(45) Date of Patent: Jul. 7, 2009

(54) CAPSULE-TYPE MEDICAL DEVICE

(75) Inventor: Junichi Ishibashi, Iruma (JP)

(73) Assignee: Olympus Corporation, Tokyo (JP)

( * ) Notice: Subject to any disclaimer, the term of this patent is extended or adjusted under 35 U.S.C. 154(b) by 33 days.

(21) Appl. No.: 11/482,088

(22) Filed: Jul. 6, 2006

(65) Prior Publication Data
US 2006/0264702 A1    Nov. 23, 2006

Related U.S. Application Data

(63) Continuation of application No. PCT/JP2004/019559, filed on Dec. 27, 2004.

(30) Foreign Application Priority Data

Jan. 7, 2004    (JP)    ............................ 2004-002426

(51) Int. Cl.
*A61B 5/05*    (2006.01)
(52) U.S. Cl. .................. 600/476; 343/908; 600/302; 600/118; 128/903
(58) Field of Classification Search ............... 600/160, 600/421–424, 549, 476, 407, 310, 106, 478, 600/114, 118, 109; 128/899; 343/908, 855, 343/879, 788
See application file for complete search history.

(56) References Cited

U.S. PATENT DOCUMENTS

| | | | |
|---|---|---|---|
| 5,604,531 A | | 2/1997 | Iddan et al. |
| 5,697,384 A | * | 12/1997 | Miyawaki et al. ............ 128/899 |
| 7,001,329 B2 | * | 2/2006 | Kobayashi et al. .......... 600/114 |
| 7,039,453 B2 | * | 5/2006 | Mullick et al. .............. 600/476 |
| 2003/0171652 A1 | * | 9/2003 | Yokoi et al. ................. 600/160 |
| 2004/0152988 A1 | * | 8/2004 | Weirich ....................... 600/473 |

FOREIGN PATENT DOCUMENTS

| | | |
|---|---|---|
| EP | 0 667 115 A1 | 8/1995 |
| JP | 2001-104241 | 4/2001 |

(Continued)

OTHER PUBLICATIONS

Sougou Densi Shuppan Sha, Arai, "New Antenna Engineering", together with a partial translation of p. 44.

(Continued)

*Primary Examiner*—Eric F Winakur
*Assistant Examiner*—Lawrence N Laryea
(74) *Attorney, Agent, or Firm*—Scully, Scott, Murphy & Presser, P.C.

(57) ABSTRACT

In order to realize a capsule-type medical device suitable for improving efficiency of wireless transmission/reception using an antenna to increase radiowave power, a capsule-type medical device is configured so as to comprise an image-capturing illumination unit in which an illumination optical system and an image-capturing unit are provided as a function executing unit for executing a predetermined function within a subject to be examined, an RF unit serving as a wireless unit for communicating a signal generated by this image-capturing illumination unit being driven, or a signal for controlling driving of the image-capturing illumination unit with the outside of the subject to be examined wirelessly, and an antenna, which is provided in this RF unit, including a pair of antenna elements formed in a tubular shape for covering the outer circumference of the image-capturing illumination unit.

13 Claims, 11 Drawing Sheets

FOREIGN PATENT DOCUMENTS

| | | | |
|---|---|---|---|
| JP | 2001-112740 | | 4/2001 |
| JP | 2001-224551 | | 8/2001 |
| JP | 2001-231744 | | 8/2001 |
| JP | 2001-245844 | * | 9/2001 |
| JP | 2003-038424 | | 2/2003 |
| JP | 2003-070728 | | 3/2003 |
| JP | 2003-366575 | * | 10/2003 |
| WO | WO 03/090618 A2 | | 11/2003 |

OTHER PUBLICATIONS

Ogawa K. et al., "An Analysis of the Effective Radiation Efficiency of the Normal Mode Helical Antenna Close to the Human Abdomen at 150 MHz", *The Institute of Electronics, Information and Communication Engineers*: AP2000-9 (Apr. 2000), pp. 55-62.

Haishi et al., "Small Plane Antenna", *The Institute of Electronics, Information and Communication Engineers*, together with a partial translation of p. 33.

* cited by examiner

_US 7,558,620 B2_

CAPSULE-TYPE MEDICAL DEVICE

CROSS REFERENCE TO RELATED APPLICATION

This application is a continuation application of PCT/JP2004/019559 filed on Dec. 27, 2004 and claims benefit of Japanese Application No. 2004-002426 filed in Japan on Jan. 7, 2004, the entire contents of which are incorporated herein by this reference.

BACKGROUND OF THE INVENTION

1. Field of the Invention

The present invention relates to a capsule-type medical device, and particularly relates to an antenna mechanism configuration to be built into a capsule-type medical device.

2. Description of the Related Art

In recent years, capsule-type medical devices have been employed in the medical field. Capsule-type medical devices do not need an insertion portion employed as with conventional endoscopes. The shape thereof is formed so as to be readily swallowed by a patient.

Following being swallowed by a patient, the conventional capsule-type medical device within the body cavity performs communication with an external unit so as to perform desired operations such as image acquisition or distribution of medicine, for example.

As for such a conventional capsule-type medical device, devices in which antenna means is provided such as described in Japanese Unexamined Patent Application Publication No. 2003-38424 and Japanese Unexamined Patent Application Publication No. 2001-224551 have been proposed, for example.

With the above Japanese Unexamined Patent Application Publication No. 2003-38424, the above antenna means is shown in the drawings, but the placement of an antenna member is not particularly described in detail.

On the other hand, the capsule-type medical device according to the above Japanese Unexamined Patent Application Publication No. 2001-224551 has a configuration wherein, in addition to providing a power-receiving antenna for receiving wireless electric power, a transmitting antenna for transmitting the image signal image-captured by built-in image-capturing means is disposed at the other end of the above power-receiving antenna.

Also, in comparison with these, as for another conventional capsule-type medical device, devices in which an antenna is provided on the outer circumference of the capsule such as described in Japanese Unexamined Patent Application Publication No. 2001-104241, Japanese Unexamined Patent Application Publication No. 2001-231744, and Japanese Unexamined Patent Application Publication No. 2003-70728, have been proposed.

With the capsule-type medical device according to the above Japanese Unexamined Patent Application Publication No. 2001-104241, a flexible antenna board is wrapped around the outer circumference of an electric component holding tube within the capsule.

Also, with the above capsule-type medical device according to the above Japanese Unexamined Patent Application Publication No. 2001-231744, with respect to the capsule-type medical device according to the above Japanese Unexamined Patent Application Publication No. 2001-104241, a shield member is further disposed inside of the above antenna. Also, with the above capsule-type medical device according to the above Japanese Unexamined Patent Application Publication No. 2003-70728, the external wall of the capsule is used as the above antenna.

With these conventional capsule-type medical devices, an antenna is disposed around the circumference of the capsule, with the antenna means being made up of an integrated antenna member.

SUMMARY OF THE INVENTION

A first capsule-type medical device according to the present invention includes function executing unit for executing a predetermined function within a subject to be examined, wireless unit for wirelessly communicating the signal generated by driving of the function executing unit, or a signal for controlling driving of the function executing unit to and from the outside of the subject to be examined, and antenna including a pair of antenna elements, which is provided on the wireless unit and formed in a tubular shape for covering the outer circumference of the function executing unit.

DETAILED DESCRIPTION OF THE PREFERRED EMBODIMENT(S)

Description will be made regarding respective embodiments of the present invention with reference to the drawings.

First Embodiment

Figure 1:
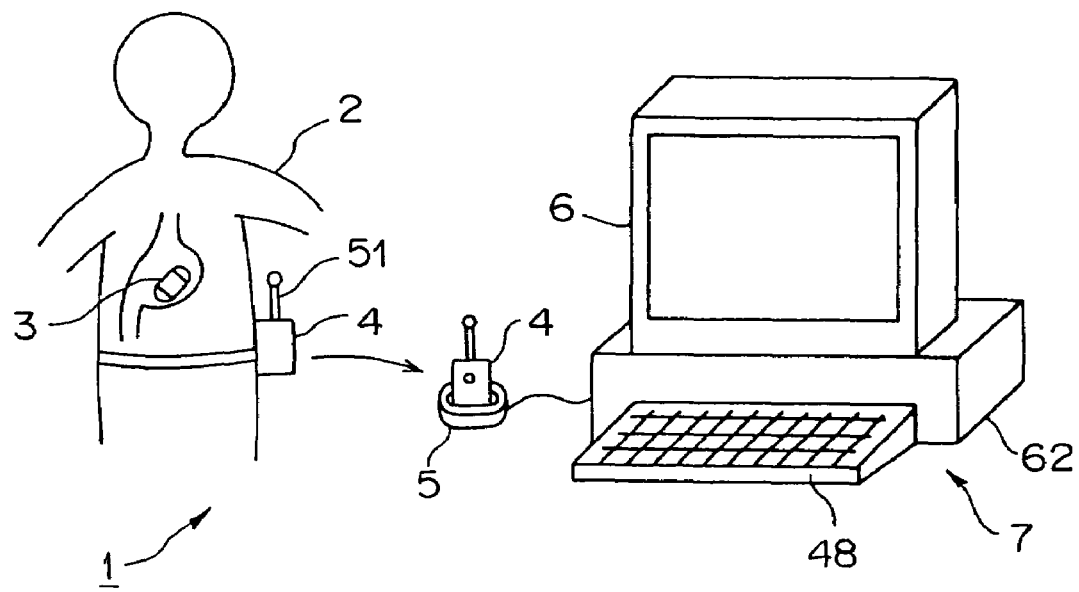
FIG. 1 is an overall configuration view of a capsule-type medical device system including a capsule-type medical device according to a first embodiment.
Figure 2:
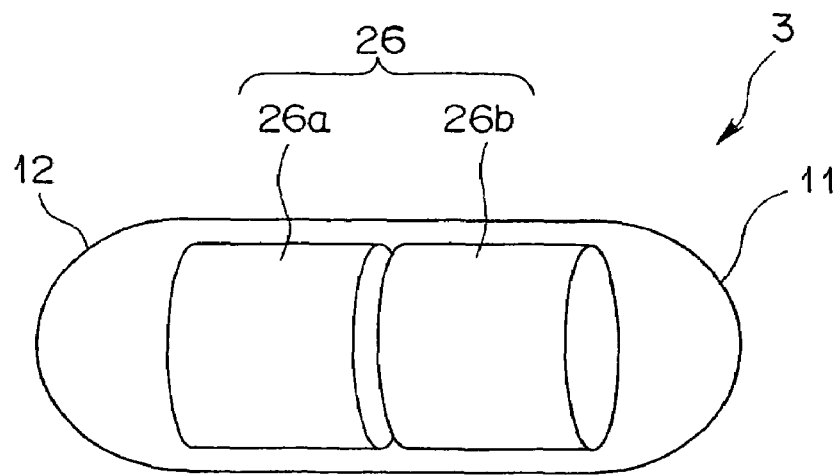
FIG. 2 is an explanatory diagram illustrating the capsule-type medical device shown in FIG. 1.
Figure 3:
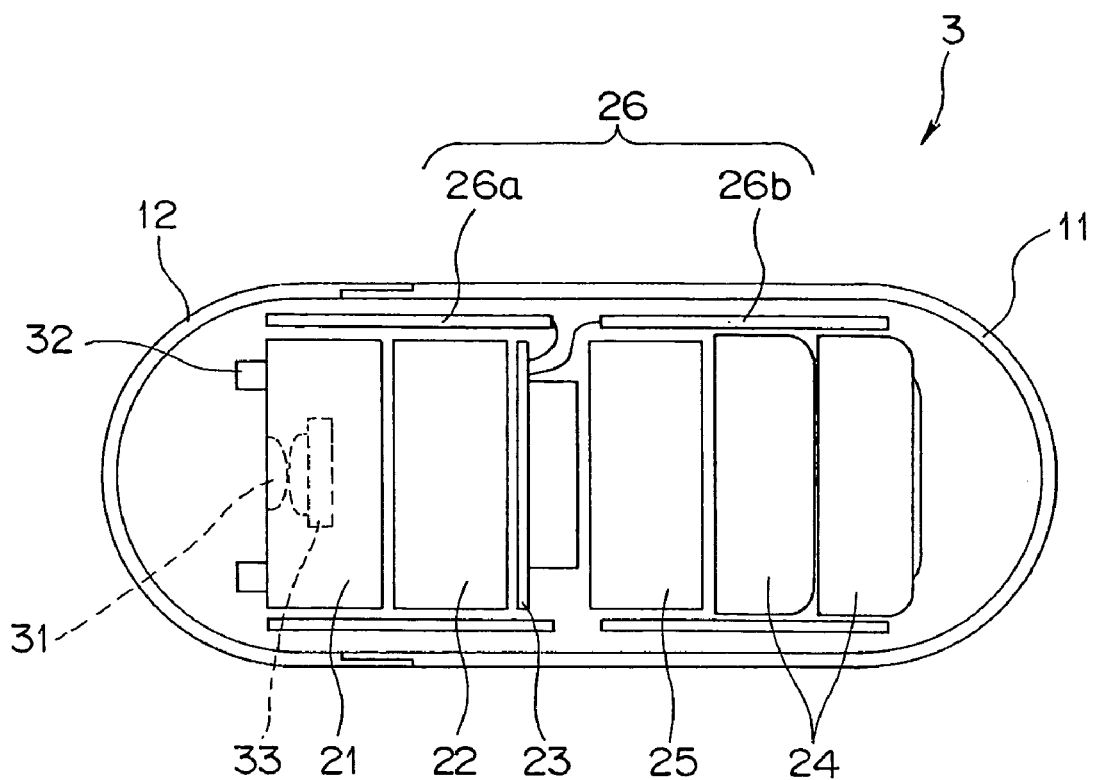
FIG. 3 is an explanatory diagram illustrating the internal configuration of the capsule-type medical device shown in FIG. 2.
Figure 4:
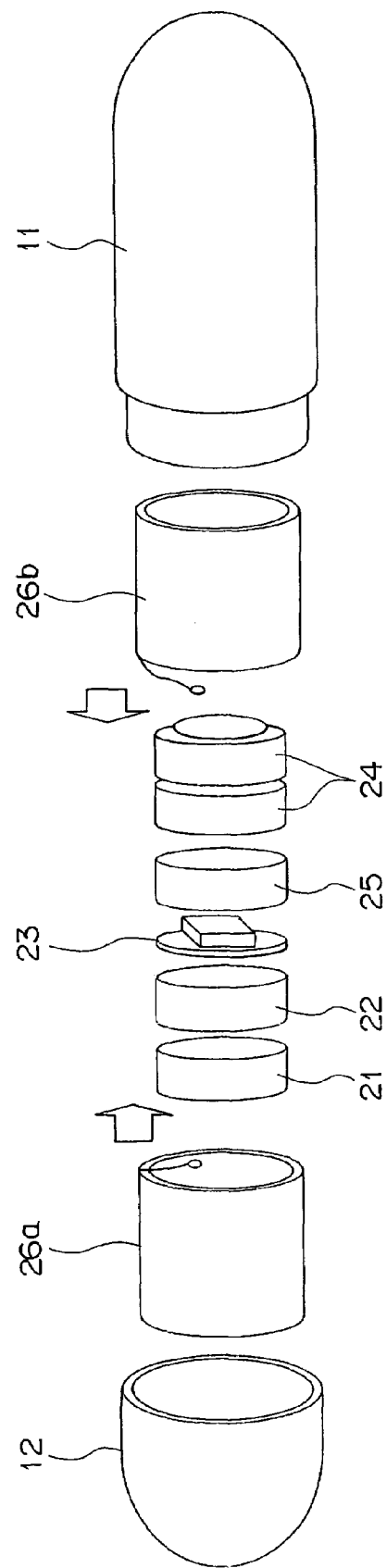
FIG. 4 is an exploded perspective view of the capsule-type medical device shown in FIG. 3.
Figure 5:
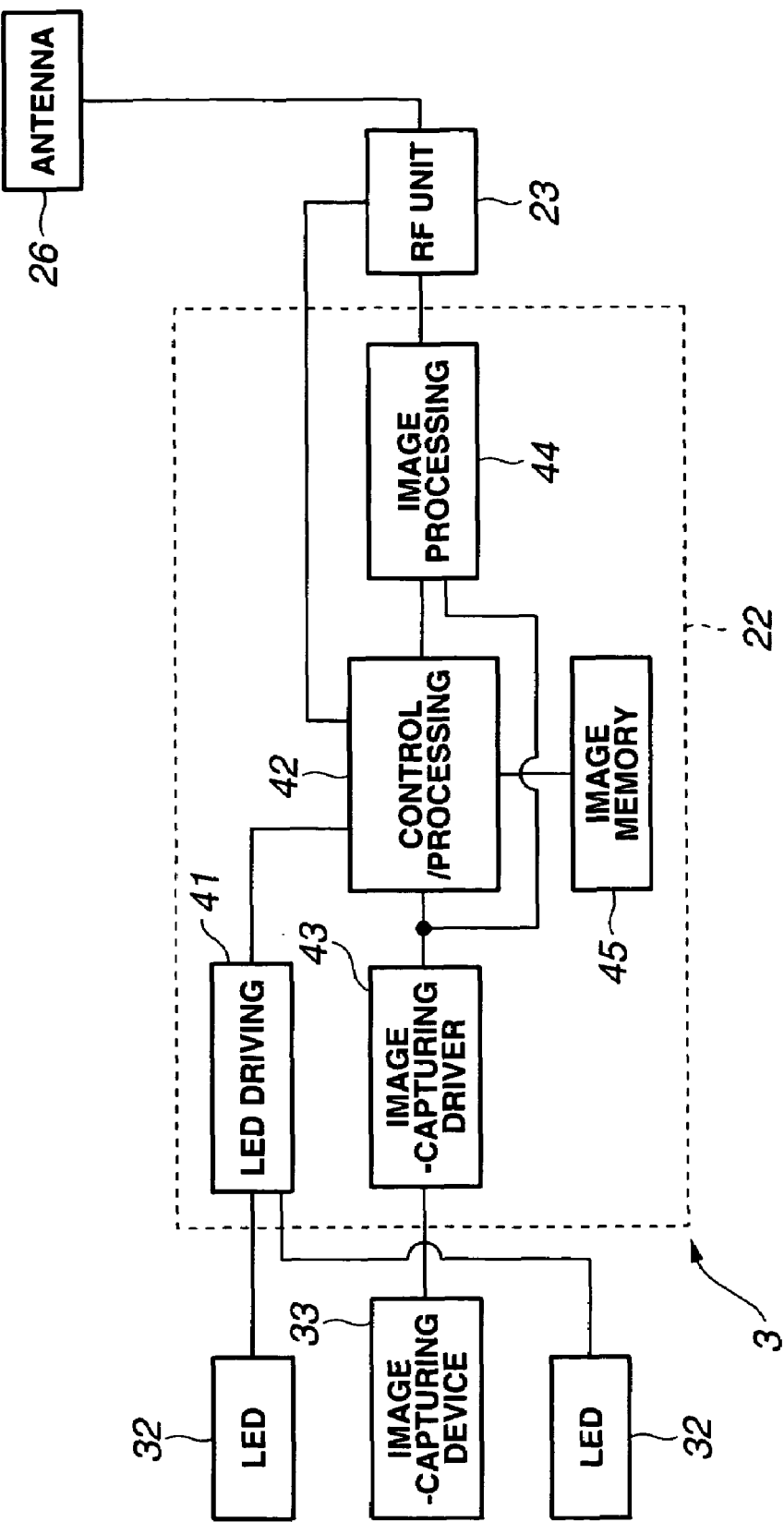
FIG. 5 is a circuit block diagram illustrating the configuration of the electric system of the capsule-type medical device.
Figure 6:
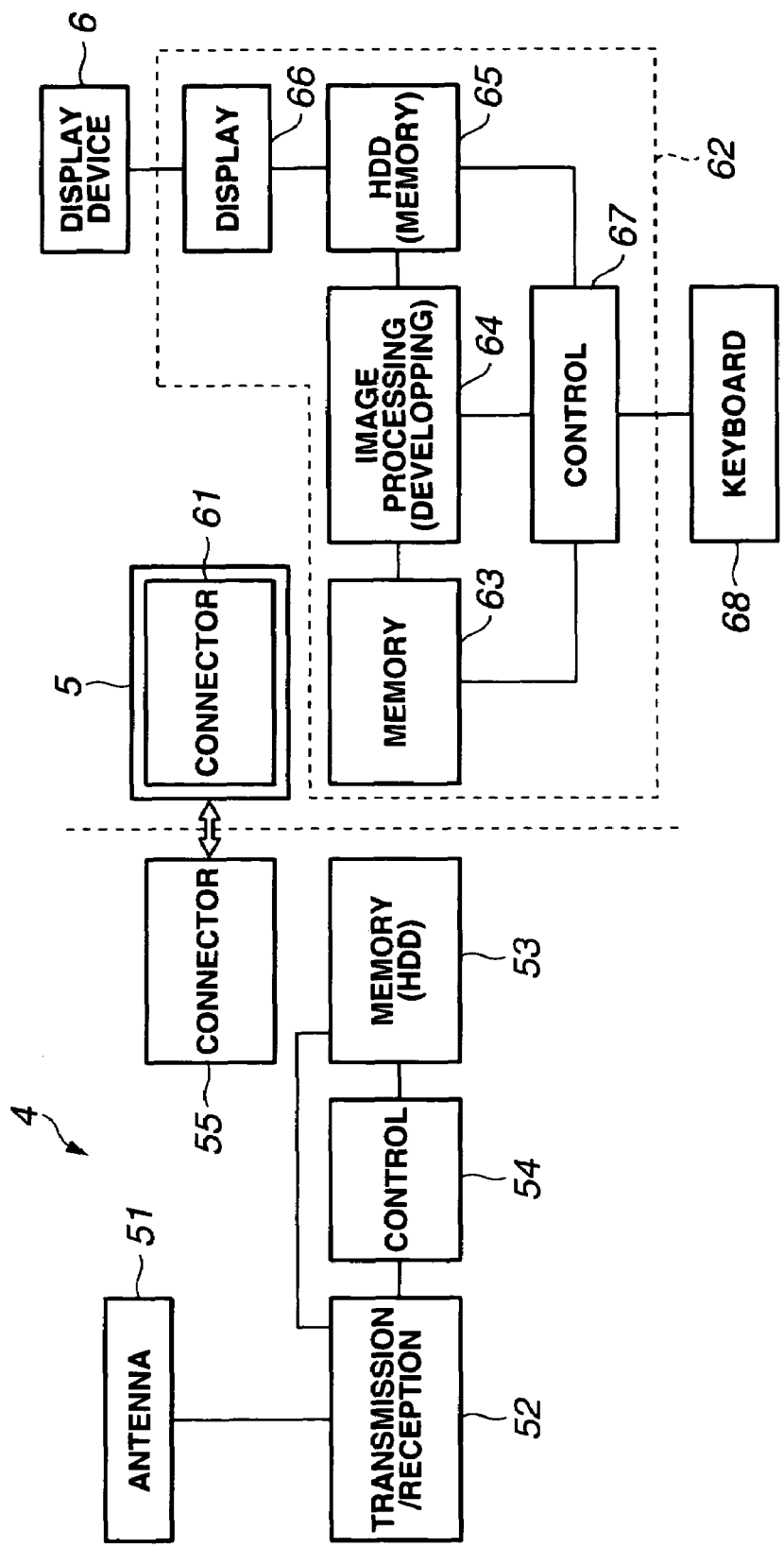
FIG. 6 is a circuit block diagram illustrating the configuration of the electric system of the external unit and display system shown in FIG. 1.
Figure 7:
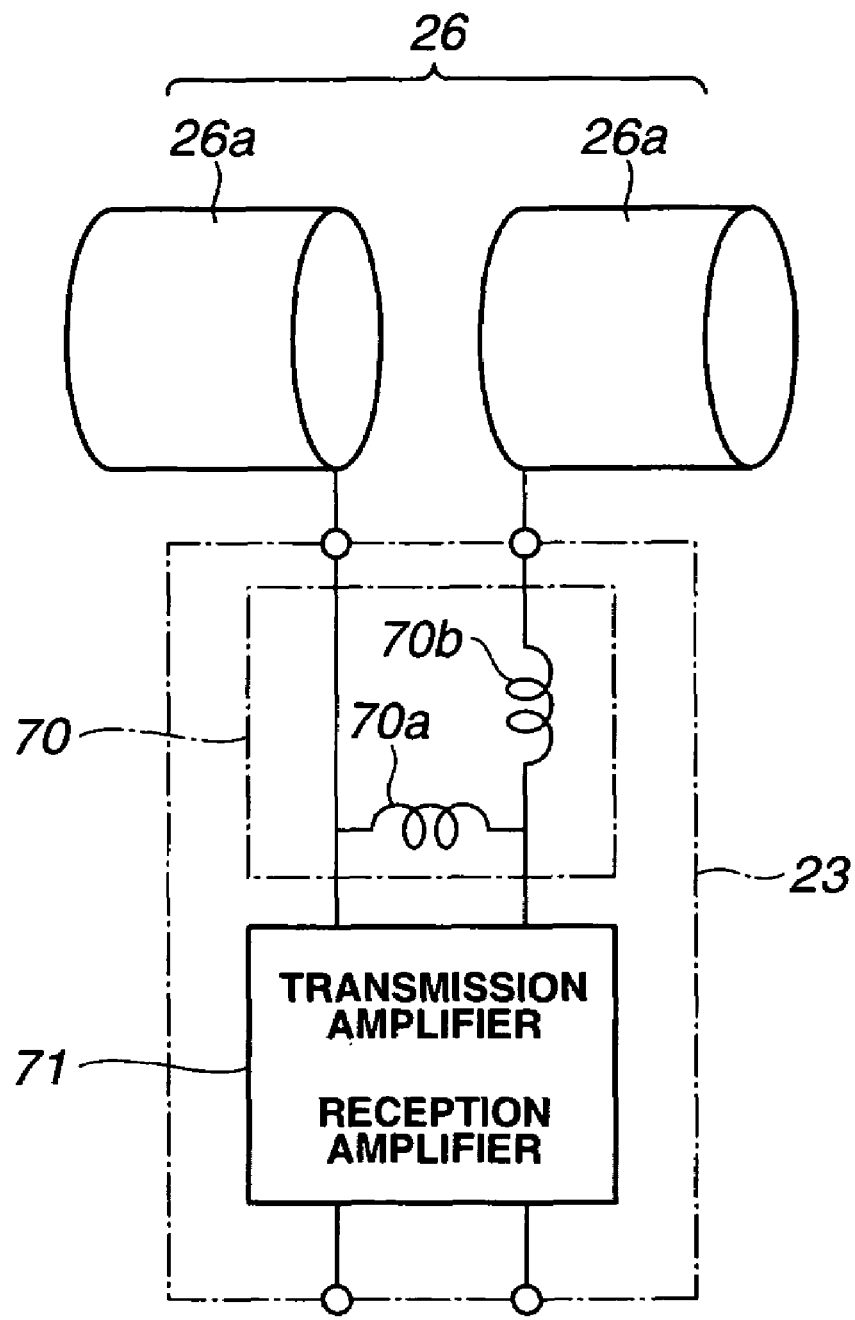
FIG. 7 is a circuit block diagram illustrating an antenna element and an antenna matching circuit.
Figure 8:
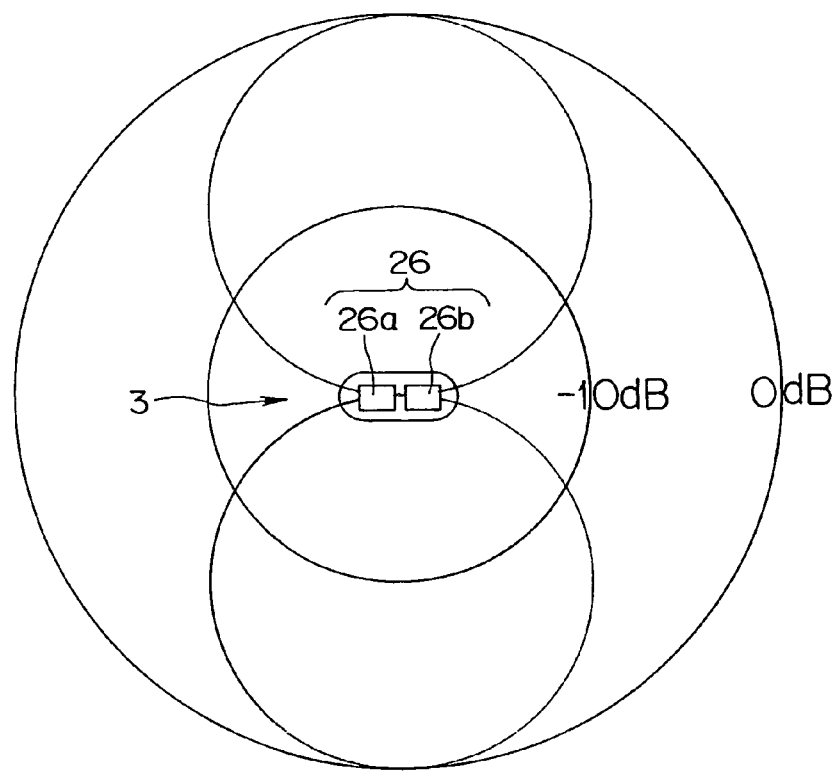
FIG. 8 is an antenna directivity properties diagram of the capsule-type medical device according to the first embodiment.
Figure 9:
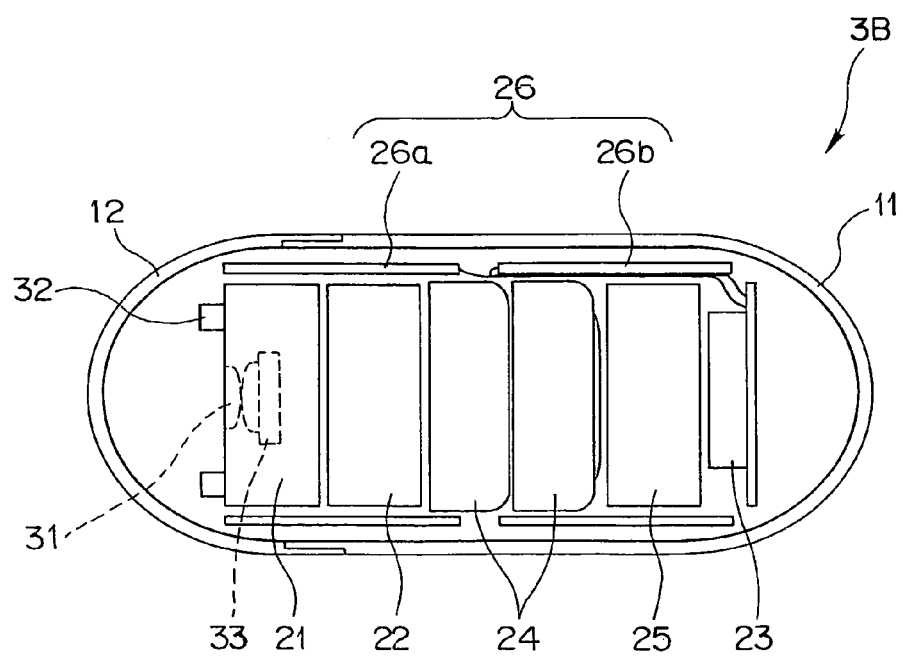
FIG. 9 is an explanatory diagram illustrating a first modification of the capsule-type medical device.
Figure 10:
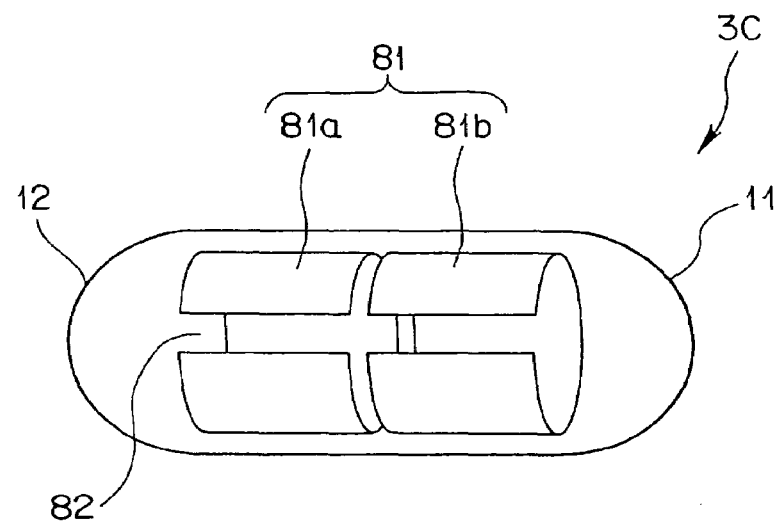
FIG. 10 is an explanatory diagram illustrating a second modification of the capsule-type medical device.

FIG. 1 through FIG. 10 relate to a first embodiment of the present invention, wherein FIG. 1 is an overall configuration view of a capsule-type medical device system including a capsule-type medical device, FIG. 2 is an explanatory diagram illustrating the capsule-type medical device shown in FIG. 1, FIG. 3 is an explanatory diagram illustrating the internal configuration of the capsule-type medical device shown in FIG. 2, FIG. 4 is an exploded perspective view of the capsule-type medical device shown in FIG. 3, FIG. 5 is a circuit block diagram illustrating the configuration of the electric system of the capsule-type medical device, FIG. 6 is a circuit block diagram illustrating the configuration of the electric system of the external unit and display system shown in FIG. 1, FIG. 7 is a circuit block diagram illustrating an antenna element and an antenna matching circuit, FIG. 8 is an antenna directivity properties diagram of the capsule-type medical device according to a first embodiment, FIG. 9 is an explanatory diagram illustrating a first modification of the capsule-type medical device, and FIG. 10 is an explanatory diagram illustrating a second modification of the capsule-type medical device.

As shown in FIG. 1, a capsule-type medical device system 1 comprises a capsule-type medical device 3 for inspecting the inside of a person to be examined 2, an external unit 4 for receiving image data from this capsule-type medical device 3, and accumulating the image data, an external-unit mounting unit 5 capable of freely detachably mounting this external unit 4, and a display system 7 for reading the signal data accumulated in this external unit 4 to display this on a display device 6.

As shown in FIG. 2 through FIG. 4, the capsule-type medical device 3 comprises a capsule frame body 11 of which both cylindrical ends are formed in a hemispheric shape so as to form a protective capsule with a transparent member 12 being provided on one end thereof.

Specifically, the capsule-type medical device 3 has a cylindrical shape of which the size and outer shape enable swallowing from the mouth and passing through the esophagus with the transparent member 12 being provided on one end thereof and the capsule frame body 11 blockaded on the other end. The one end of this capsule frame body 11 has a domed shape covered with the transparent hemispheric-shaped transparent member 12.

The capsule frame body 11 includes an image-capturing illumination unit 21 in which an illumination system and an image-capturing unit are provided as function executing unit, a signal processing unit 22 for performing signal processing of the image (video) signal captured by the image-capturing illumination unit 21 and control of the entire capsule, an RF unit 23 serving as wireless unit for modulating the image signal subjected to signal processing by this signal processing unit. 22 to convert this into a transmitting signal, or demodulating a signal from the outside to propagate this to the signal processing unit 22, a power supply unit 25 for supplying electric power to the respective units within the capsule from a battery 24, and an antenna 26 serving as antenna, which is provided in the RF unit 23, for wirelessly transmitting the signal generated by driving of the function executing unit to the outside.

The image-capturing illumination unit 21 serving as a function executing unit is stored at the center of one end (serving as the observation side) surface of the capsule frame body 11. Further specifically, an object lens 31 making up the image-capturing optical system is attached to the center of one end (serving as the observation side) surface of the capsule frame body, and at the multiple portions, e.g., four portions around thereof multiple LEDs 32 serving as illumination optically systems are attached, thereby illuminating the field-of-view range by the object lens 31. Also, at the image forming position of the object lens 31 of the image-capturing illumination unit 21, a solid-state image-capturing device 33 such as a CMOS (Complementary Metal Oxide Semiconductor) or CCD (Charge Coupled Device) is attached.

The signal processing unit 22 is disposed backward the image-capturing illumination unit 21. The detailed configuration of this signal processing unit 22 will be described later. The RF unit 23 serving as a wireless unit is disposed backward the signal processing unit 22. This RF unit 23 comprises a transmission amplifier and a reception amplifier which are not shown in the drawing. Also, the power supply unit 25 is disposed backward this RF unit 23.

Also, the antenna 26 comprises two cylindrical electroconductive members, an antenna element 26a and an antenna element 26b. The antenna elements 26a and 26b of the antenna 26 are disposed so as to cover the image-capturing illumination unit 21, signal processing unit 22, RF unit 23, battery 24, and power supply unit 25 around the axis of the cylindrical capsule frame body 11. Note that though not shown in the drawing, between the respective built-in components are disposed wiring of signal lines for electrically connecting each of those, electric power supply, and so forth.

FIG. 5 illustrates the configuration of the electric system of the capsule-type medical device 3 in further detail.

The LEDs 32 are driven by an LED driving circuit 41 to illuminate inside the human body by emitting light with white light. The LED driving circuit 41 is controlled by the control signal from a control/processing circuit 42.

The reflected light of a subject illuminated by the LEDs 32 is captured by the object lens 31, and is image-formed on the image-capturing surface of the solid-state image-capturing device (hereinafter, simply referred to as image-capturing device) 33 as a subject image. Subsequently, the subject image is captured by the image-capturing device 33, and is subjected to photoelectric conversion.

With this image-capturing device 33, the photoelectrically-converted signal is read out by the drive signal from the image-capturing driver 43, and is input to an image processing circuit 44 passing straight through the image-capturing driver 43. Note that the image-capturing driver 43 and image processing circuit 44 operate under control of the control/processing circuit 42.

The image signal subjected to signal processing by the image processing circuit 44 is temporarily accumulated in the image memory 45. Subsequently, the image signal read out sequentially from the image memory 45 is modulated with high frequency (e.g., 300 MHz) via the RF unit 23, and is transmitted from the antenna 26 to the external unit 4 side.

On the other hand, the external unit 4 which receives the image data or the like from the capsule-type medical device 3 has, for example, a box or cylindrical shape including the antenna 51, and is configured so as to be attached to the abdomen of a person to be examined 2 using a belt or the like.

The configuration of the electric system of this external unit 4 is shown in FIG. 6.

The signal received at the antenna 51 is demodulated by the transmission/reception circuit 52, and the demodulated image data is stored in the memory 53 (a hard disk may be employed instead of the memory 53, which is abbreviated as HDD in FIG. 6 or the like). The transmission/reception circuit 52 and memory 53 are controlled by the control circuit 54. Also, the control circuit 54 converts the image signal received at the antenna 51 and demodulated into digital image data, and then performs a control operation for writing this into the memory 53.

Also, the memory 53 is connected to a connector 55, and the image data stored in the memory 53 is configured so as to be output via this connector 55. This connector 55 can be freely detachably mounted on the connector 61 of the external-unit mounting unit 5, and upon being mounted, the image data in the memory 53 can be transferred to a personal computer main unit 62 side making up a display system 7.

This personal computer main unit 62 comprises memory 63, which is connected to the connector 61 for example, serving as a buffer for temporally storing image data, an image processing circuit 64, which is connected to this memory 63, for performing processing such as rendering of image data, a hard disk (or memory) 65, which is connected to the image processing circuit 64, for storing the developed image data, a display circuit 66, which is connected to the hard disk 65, for converting the stored image data into a display signal, and a control circuit 67 for controlling the memory 63, image processing circuit 64, and hard disk 65. The image according to the display signal from the display circuit 66 is displayed on a display device 6.

Also, the control circuit 67 is connected to a console such as a keyboard 68, and upon an instruction such as that image display is input from the keyboard 68, the control circuit 67 performs display of the image instructed or the like.

The operations in the case in which the capsule-type medical device 3 has only a transmission function have been mentioned above. However, in a case in which the capsule-type medical device 3 has a transmission/reception function, the capsule-type medical device 3 operates while communicating with the external unit 4. In this case, the control circuit 54 of the external unit 4 performs control operations for transmitting a control signal for causing the capsule-type medical device 3 side to start image capturing from the antenna 51 via the transmission/reception circuit 52.

The capsule-type medical device 3 receives this control signal at the antenna 26, demodulates this at the RF unit 23, and transmits this to the control/processing circuit 42. Upon the control/processing circuit 42 identifying that the received signal is a control signal for starting image capturing (by comparing to or referencing the data stored in the internal memory or the like beforehand), the control/processing circuit 42 operates the LED driving circuit 41, image-capturing driver 43, image processing circuit 44, and RF unit 23 in an intermittent manner, for example.

For example, the control/processing circuit 42 controls the LEDs 32 to emit light for 1/30 seconds once per 1 second or so, after 1/30 seconds thereof controls the image-capturing driver 43 to apply a driving signal to the image-capturing device 33 and read out the signal image-captured, controls the image processing circuit 44 to subject the readout signal to image processing to convert this into a compressed image signal, and controls the RF unit 23 to subject the signal to high-frequency modulation, and controls the antenna 26 to transmit the signal.

This and subsequent operations are the same as those of the above capsule-type medical device 3 having only a transmission function.

Note that in the event of the capsule-type medical device 3 including a transmission/reception function, the transmission functions of the image-capturing illumination unit 21 and RF unit 23 are set to a sleep mode while no control signal is transmitted from the external unit 4 so as to suppress the electric power consumption of the capsule-type medical device 3.

Now, the antenna employed for the conventional capsule-type medical devices is expected to operate as an antenna member similar to a monopole antenna which needs a great bottom plate structure portion as compared with the wavelength thereof. If such a monopole antenna is built in the capsule-type medical device, the size of the bottom plate to be built in is consequently reduced, and this causes the bottom plate to serve an insufficient role. In this case, it is difficult for the conventional capsule-type medical devices to emit radiowaves outside the human body, resulting in the possibility of deterioration of efficiency in wireless transmission/reception using the antenna.

With the present embodiment, as described above, the antenna 26 is made up of the two members of the antenna elements 26a and 26b, which has a dipole antenna structure.

Further specifically, the antenna elements 26a and 26b have a diameter greater than the respective built-in components (image-capturing illumination unit 21, signal processing unit 22, RF unit 23, battery 24, and power supply unit 25) of the capsule-type medical device 3, and also are formed in a hollow cylindrical shape using an electric conductor such as aluminum or copper. Note that the antenna elements 26a and 26b may be made up of any other material other than aluminum and copper as long as an electric conductor equivalent to a common antenna material.

These two members of the antenna elements 26a and 26b can be employed as a common dipole antenna by being disposed in the longitudinal direction of the capsule-type medical device 3.

Now, as for the Michaelis constant of a medium within the human body, relative permittivity is around 50 through 60, permeability is almost the same as open space. Accordingly, the wavelength reduction ratio is around $1/7$ ($\cong 1/\sqrt{(55)}$), and if the utilized frequency of radiowaves is 310 MHz for example, the wavelength within the human body is around 13 cm.

With the two members of the antenna elements 26a and 26b, the antenna length is set to around 20 mm so as to be employed for a dipole antenna of which wavelength is shortened by 15% or so. Accordingly, the two members of the antenna 26a and 26b result in operating in a state close to a known infinitesimal dipole antenna.

Here, the input impedance Zi within the free space of the infinitesimal dipole antenna is as follows.

Expression 1

$$Zi = 80(k_0 h)^2 - j\frac{120}{k_0 h}\left(\ln\left(\frac{h}{a}\right) - 1\right)[\Omega] \quad (1)$$

Here, k0 denotes a wave number, h denotes ½ of a dipole antenna length, and a denotes an antenna axial radius ("New Antenna Engineering" written by Arai, Sougou Densi Shuppan Sha Page 44). It can be understood from the above Expression (1) that with the impedance of a dipole antenna, the shorter the antenna size is, the smaller the resistance value, and the greater the reactance value. It can be expected to have the same impedance behavior even within the human body.

On the other hand, upon the antenna being operated near the human body, it has been known that antenna gain is excessively deteriorated (The Institute of Electronics, Information and Communication Engineers: AP2000-9(2000-04) "An Analysis of the Effective Radiation Efficiency of the Normal Mode Helical Antenna Close to the Human Abdomen at 150 MHz" written by Ogawa and others).

It has been known that this is because moving the antenna close to the human body increases reactance and causes impedance mismatching, resulting in deterioration of antenna gain. Accordingly, even in the event of the capsule-type medical device 3 including such an antenna, the device is driven within the human body, and consequently, the device is affected in the same way.

However, with the capsule-type medical device 3 according to the present embodiment, according to Expression (1), forming the axial diameter 2a of the antenna elements 26a and 26b (of the dipole antenna) thick can decrease the reactance of input impedance of the antenna 26.

Accordingly, with the capsule-type medical device 3 according to the present embodiment, the size of the diameter of the antenna elements 26a and 26b is set close to the diameter value of the capsule-type medical device 3, so the advantage for decreasing the above reactance can be expected. Accordingly, as for the impedance matching of the antenna elements 26a and 26b, the inductance value of an inductor for canceling out the reactance value can be decreased, and consequently, impedance matching circuit loss can be reduced, i.e., the advantage for raising antenna efficiency can be expected.

Generally, enlarging an antenna area increases the radiation power from an antenna.

The entire radiation power Pr of a dipole antenna within free space is

Expression 2

$$Pr = \frac{2\pi\eta_0}{3}\left(\frac{Il}{\lambda_0}\right)^2 \quad (2)$$

Here, η0 denotes characteristic impedance in the air, I denotes electric current, l (=2h) denotes an antenna length, and λ0 denotes a wavelength ("Small Plane Antenna" written by Haishi and others, The Institute of Electronics, Information and Communication Engineers, P33). The same impedance behavior can be expected within the human body as well.

As can be understood from the above Expression (2), upon enlarging the antenna of a dipole antenna, the radiation power thereof also increases. For example, the magnitude of the entire radiation power differs four times (6 dB) between the antenna length of 20 mm and the antenna length of 10 mm.

Moreover, great decay of radiowaves occurs within the human body, so in order to realize appropriate transmission/reception, it is effective to enlarge the antenna size so as to raise antenna efficiency.

However, in order to apply this antenna to the capsule-type medical device 3, it is necessary to configure this antenna as small as possible.

With the present embodiment, as described above, an arrangement is made wherein the diameters of the antenna elements 26a and 26b are formed greater than the respective built-in components (image-capturing illumination unit 21, signal processing unit 22, RF unit 23, buttery 24, and power supply unit 25) of the capsule-type medical device 3, thereby covering the respective built-in components of the capsule-type medical device, and accordingly, the antenna size can be enlarged as close to the capsule size as possible, thereby improving antenna efficiency.

Now, the antenna 26 according to the present embodiment has a low resistance value regarding antenna input impedance, so a common output device of which output impedance is adjusted at 50Ω cannot be employed.

Accordingly, the present embodiment provides an antenna matching circuit 70 for performing impedance matching of the antenna 26.

As shown in FIG. 7, the antenna matching circuit 70 is provided within the RF unit 23. The antenna matching circuit 70 is disposed between the antenna element 26a and antenna element 26b, and at the same time between these antenna elements 26a and 26b and the transmission amplifier and reception amplifier 71 of the RF unit 23.

The antenna matching circuit 70 is connected to and made up of an inductance 70a having a high Q (load) of 10 nH through 20 nH or so, and further an inductance 70b having the same load as the above at one antenna element side. The antenna matching circuit 70 performs known impedance matching as to the antenna 26 to improve antenna efficiency thereof.

Note that if the capsule-type medical device 3 is exclusive to transmission, there is a method for directly driving the antenna 26 by suppressing the device output of the transmission amplifier to low impedance. In this case, the antenna 26 is arranged to connect to the amplifier via the inductance 70b for decreasing the reactance of antenna input impedance.

The antenna 26 according to the present embodiment has the same directivity as a common dipole antenna. The directional characteristics of the antenna 26 is shown in FIG. 8.

As shown in FIG. 8, the antenna 26 according to the present embodiment has a letter 8-shaped directional characteristics within two dimensions with respect to the long axis of the capsule-type medical device 3, and has a doughnut-shaped directional characteristics around the axis as viewed three-dimensionally.

Thus, the capsule-type medical device 3 according to the present embodiment can have a constant radiowave emission pattern regardless of the rotational angle of the capsule long axis even if the direction to turn to is changed at each portion within the human body when moving within the human body since the antenna 26 has a dipole antenna structure, and also has an arrangement of employing a diameter greater than the diameters of the respective built-in components other than the antenna 26 (image-capturing illumination unit 21, signal processing unit 22, RF unit 23, battery 24, and power supply unit 25) to cover those built-in components, as described above.

Accordingly, the capsule-type medical device 3 according to the present embodiment can transmit/receive a wireless communication signal to and from the external unit 4 with stable signal strength having little fluctuation.

Note that the capsule-type medical device may be configured by changing the allocations of the respective built-in components other than the antenna.

As shown in FIG. 9, a capsule-type medical device 3B has a configuration wherein the battery 24 is disposed around the center to change the center of gravity of the capsule.

In this case, with the capsule-type medical device 3B, the wiring from the RF unit 23 to the antenna 26 is performed so as to pass through within the cylinder of the antenna 26, i.e., inside of the tubular antenna 26.

As for this wiring, a thick wiring material made up of as thick a copper wire as possible is employed to reduce transmission loss, though it exists within the antenna 26, and does not serve as an antenna. Note that though not shown in the drawing, not only the battery 24 but also other internal parts other than the antenna may be disposed at an arbitrary position.

Also, with the present embodiment, the tubular antenna 26 is provided, but an arrangement may be made wherein this antenna shape is modified.

As shown in FIG. 10, a capsule-type medical device 3C is configured so as to form slit portions 82 in an antenna 81 (antenna elements 81a and 81b). With the slit portions 82, internal wiring such as signal information propagation and power supply of the respective built-in components other than the antenna 81 may be disposed.

Accordingly, with the capsule-type medical device 3C, disposing internal wiring in the slit portion 82 enables internal wiring to be integrated, and also the complexity of internal wiring to be reduced.

Also, though not shown in the drawing, as for the shape of the antenna 81, the tubular shape thereof is not restricted to a cylindrical shape, rather, unevenness of the surface may be formed to dispose the internal wiring.

Further, as for the shape of the antenna 81, though not shown in the drawing, a hole may be formed in a part thereof so as to protrude an arm for operation such as medical care and tissue sampling, or so as to form a body-fluid checking uptake opening or an exhaust nozzle for dosage treatment (medicine distribution).

Also, with the present embodiment, the image-capturing device such as a CCD or CMOS sensor which captures a subject to be examined image is provided as function executing unit for executing a predetermined function within a subject to be examined, but the present invention is not restricted to this, and a pH sensor may be provided instead of the image-capturing device.

Second Embodiment

Figure 11:
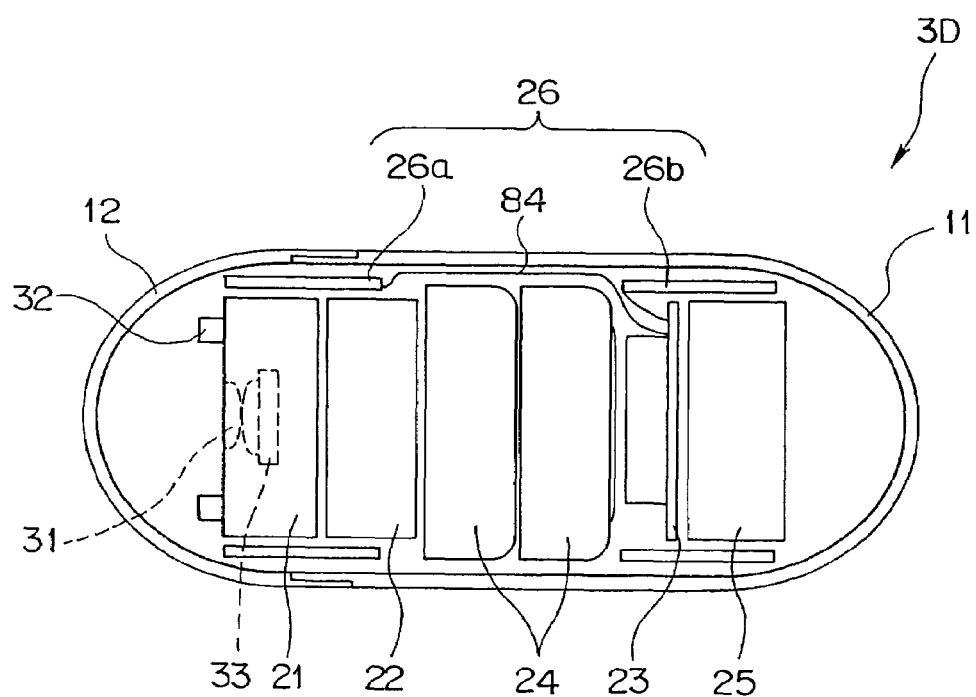
FIG. 11 is an explanatory diagram illustrating the internal configuration of a capsule-type medical device according to a second embodiment.

FIG. 11 is an explanatory diagram illustrating the internal configuration of a capsule-type medical device according to a second embodiment of the present invention.

The capsule-type medical device according to the second embodiment has a configuration wherein the above pair of antenna elements are disposed with an interval of the length equal to or more than one antenna element therebetween. The configurations other than this are the same as the above first embodiment, so the description thereof is omitted, and description will be made by appending the same reference numerals to the same configurations.

That is to say, as shown in FIG. 11, a capsule-type medical device 3D according to the second embodiment has a configuration wherein the above pair of antenna elements 26a and 26b formed in a tubular shape are disposed in the axial direction of the tubular shape, i.e., in the longitudinal direction with a mutual interval of the length equal to or more than one antenna element therebetween.

For example, with the capsule-type medical device 3D, assuming that the antenna element length of the antenna elements 26a and 26b is 6 mm, these antenna element 26a and antenna element 26b are disposed on both ends with an interval of 8 mm.

With the capsule-type medical device 3D thus configured, the antenna 26 can serve as a dipole antenna in the same way as the first embodiment, and also the battery 24 having a large part size, e.g., a size close to an approximately capsule diameter can be disposed between the antenna elements 26a and 26b.

Thus, with the capsule-type medical device 3D according to the second embodiment, an arrangement may be made wherein the antenna elements 26a and 26b are separated, with a built-in part of maximal size being disposed at the center therebetween.

Accordingly, with the capsule-type medical device 3D according to the second embodiment, in addition to obtaining the same advantages as the first embodiment, the size of capsule diameter can be reduced, thereby realizing reduction in size.

Note that as for contribution to serving as an antenna, the wiring 84 from the RF unit 23 to the antenna elements 26a and 26b contributes less when comparing the area of the antenna element with the wiring area. Also, the other exposed parts which have the possibility of serving as antenna components are outward-mounted faces of parts such as the battery 24, but a power supply filter or the like for shielding high-frequency signals is generally inserted therein, and consequently, these have less antenna effect.

Accordingly, as for an antenna, enlarging an antenna element portion increases the radiowave radiation area, so even in the event of disposing both antenna elements 26a and 26b in isolation, it is effective to enlarge the size of antenna elements as large as possible.

Third Embodiment

Figure 12:
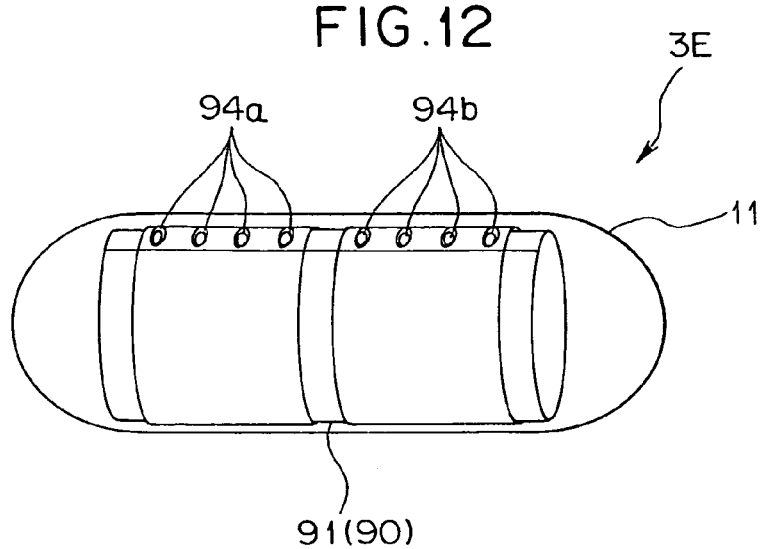
FIG. 12 is an explanatory diagram illustrating a capsule-type medical device according to a third embodiment.
Figure 13:
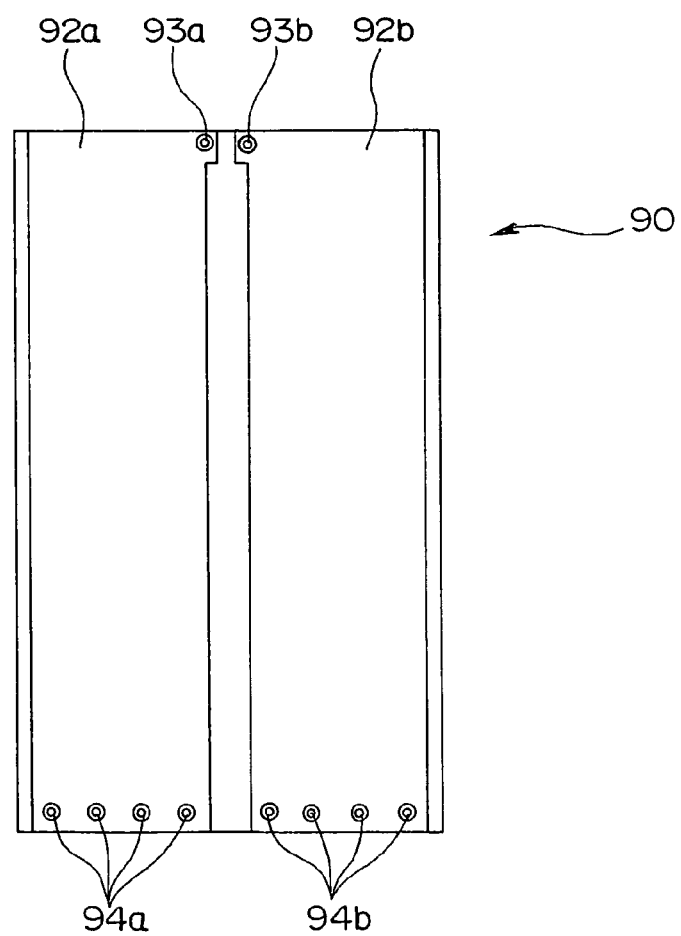
FIG. 13 is an opened view illustrating an antenna board making up the antenna element shown in FIG. 12.

FIG. 12 and FIG. 13 relate to a third embodiment of the present invention, FIG. 12 is an explanatory diagram illustrating a capsule-type medical device according to the third embodiment, and FIG. 13 is an opened view illustrating an antenna board making up the antenna element shown in FIG. 12.

While the above first and second embodiments configure an antenna using a pair of antenna elements, the third embodiment configures an antenna by forming a pair of antenna elements on one antenna board. The other configurations other than this are the same as those in the above first embodiment, so description thereof will be omitted, and description will be made by giving the same reference numerals to the same configurations.

That is to say, as shown in FIG. 12 and FIG. 13, the capsule-type medical device 3E according to the third embodiment configures an antenna 91 wherein an antenna board 90 flexibly formed from polyimide or the like is wrapped in a tubular shape. The antenna board 90 is made up of one board, and is configured so as to dispose two sheets of electroconductive films 92a and 92b thereupon in parallel.

A capsule-type medical device 3E is configured so as to wrap the antenna board 90 in a tubular shape, and dispose this so as to wrap and surround respective built-in components (image-capturing illumination unit 21, signal processing unit 22, RF unit 23, battery 24, and power supply unit 25) within this antenna board 90.

In the antenna board 90, through-hole portions 93a and 93b are provided for subjecting the RF unit 23 and electroconductive films 92a and 92b to wiring. Also, in the antenna board 90, multiple through-hole portions 94a and 94b are provided for each of the electroconductive films 92a and 92b for electrically connecting both end edges of the antenna board 90 when wrapping the antenna board 90 in a tubular shape.

The antenna board 90 is formed flexibly, so this contacts to the internal circumferential surface of the capsule frame body 11 due to elastic force when wrapping and disposing the antenna board 90. At this time, at a portion where the antenna board 90 is to be overlapped, through-hole portions 94a and 94b are electrically in contact with electroconductive films 92a and 92b close to through-hole portions 93a and 93b on the surface of the opposite side to form a cylindrical antenna.

In this case, with the antenna board 90, the overlapped portions of the through-hole portions 94a and 94b and the electroconductive films 92a and 92b may be soldered to ensure electroconductivity. Also, with the antenna board 90, the overlapped portions may be connected with a copper tape or the like.

Thus, with the capsule-type medical device 3E according to the third embodiment, in addition to the same advantages as the first embodiment, antenna is configured in a board shape, so it is unnecessary to take positioning between a pair of antenna elements into consideration, thereby improving assembling in manufacturing, and facilitating configuration.

Fourth Embodiment

Figure 14:
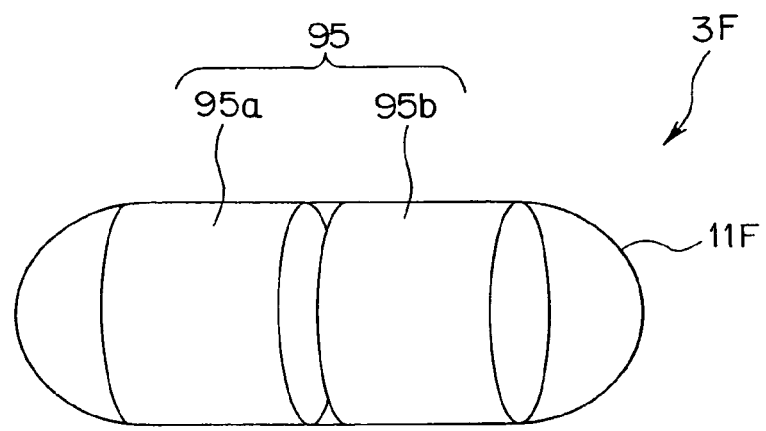
FIG. 14 is an explanatory diagram illustrating a capsule-type medical device according to a fourth embodiment.
Figure 15:
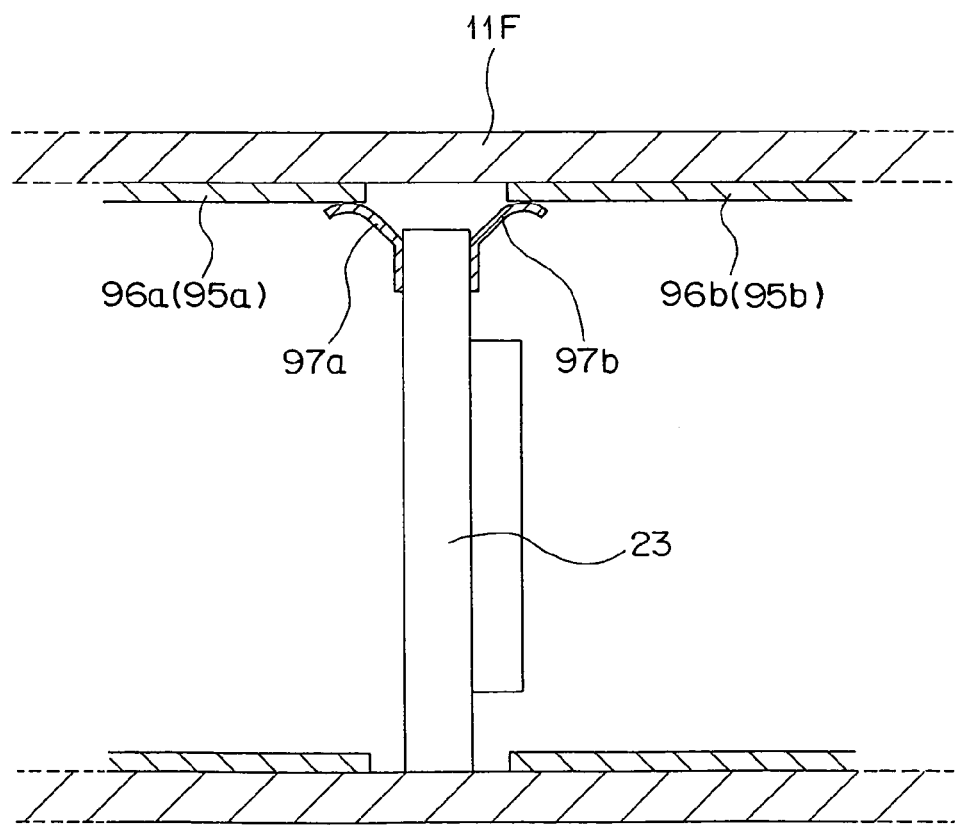
FIG. 15 is an enlarged sectional view illustrating a vicinity of the antenna shown in FIG. 14.
Figure 16:
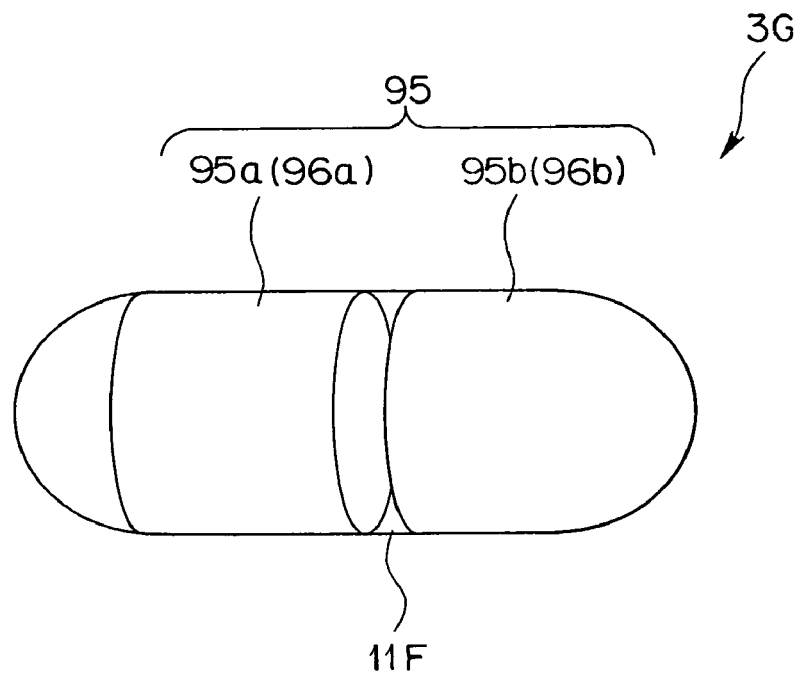
FIG. 16 is an explanatory diagram illustrating a first modification of the capsule-type medical device shown in FIG. 14.
Figure 17:
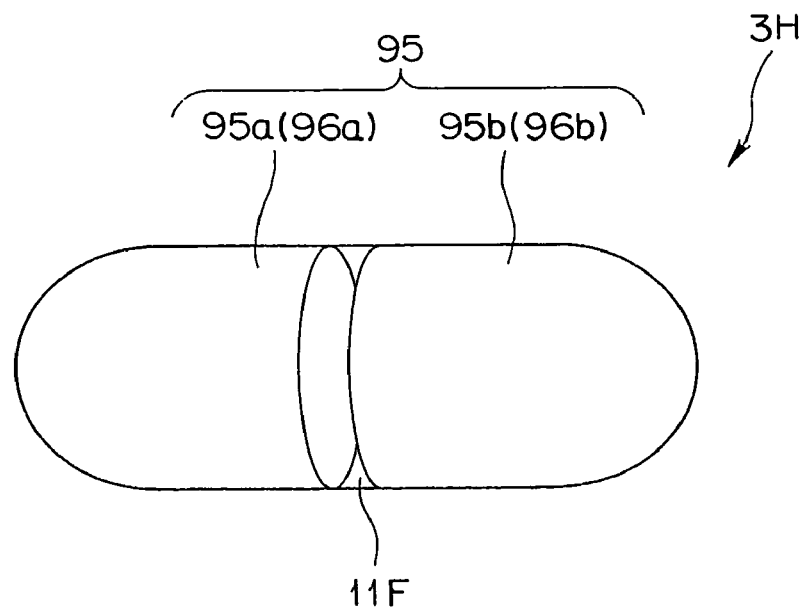
FIG. 17 is an explanatory diagram illustrating a second modification of the capsule-type medical device shown in FIG. 14.

FIG. 14 through FIG. 17 relate to a fourth embodiment of the present invention, FIG. 14 is an explanatory diagram illustrating a capsule-type medical device according to the fourth embodiment, FIG. 15 is an enlarged sectional view illustrating the vicinity of the antenna shown in FIG. 14, FIG. 16 is an explanatory diagram illustrating a first modification of the capsule-type medical device shown in FIG. 14, and FIG. 17 is an explanatory diagram illustrating a second modification of the capsule-type medical device shown in FIG. 14.

While the above third embodiment configures the pair of antenna elements by forming electroconductive films 92a and 92b on the antenna board 90, the fourth embodiment configures the pair of antenna elements by forming two electroconductive membranes on the internal wall (inner circumferential surface) of a capsule frame body. The other configurations other than this are the same as those in the above first embodiment, description thereof will be omitted, and description will be made by giving the same reference numerals to the same configurations.

That is to say, as shown in FIG. 14, a capsule-type medical device 3F according to the fourth embodiment is integrally formed into a capsule frame body 11F, and an antenna 95 wherein a pair of antenna elements 95a and 95b are formed with later-described two electroconductive membranes is provided on the inner wall (inner circumferential surface) of this capsule frame body 11F.

Note that with the present embodiment, the capsule frame body 11F is formed with a transparent member, but the other portions other than the portion where the image-capturing illumination unit 21 is disposed may be formed with a transparent member. Also, the capsule frame body 11F may be a capsule of which the entirety is opaque if the capsule-type medical device 3F is an application capsule for such as treatment or tissue sampling, other than image-capturing of an object.

Next, the detailed configuration of the antenna 95 according to the present embodiment will be described.

As shown in FIG. 15, with the antenna 95 according to the present embodiment, the pair of antenna elements 95a and 95b are configured by electroconductive membranes 96a and 96b being formed on the inner wall (inner circumferential surface) of the capsule frame body 11F so as not to contact with each other, e.g., with an interval of 2 mm or so. Note that FIG. 15 illustrates a wiring between the RF unit 23 and the antenna elements 95a and 95b.

Connection wiring for transmission/reception between the antenna elements 95a and 95b and the RF unit 23 is connected to each of the electroconductive membranes 96a and 96b of the antenna elements via two contact terminals 97a and 97b having a spring function (pressing force) each attached to the front surface and the back surface of the board of the RF unit 23. The contact terminals 97a and 97b are pressed downwards by pressing force when facing the drawing, the electroconductive membranes 96a and 96b making up the antenna 95a and 95b are pressed and fixed on the inner wall (inner circumferential surface) side of the capsule frame body 11F by the reaction force thereof.

Though not shown in the drawing, the other built-in components other than the antenna are provided in the same way as the first embodiment, and are held with holding tools (not shown) so as to maintain the allocation relations between the respective built-in components. Accordingly, with the capsule-type medical device 3F according to the present embodiment, as with the above description in the first embodiment, the respective built-in components other than the antenna elements 95a and 95b are inserted while being held, thereby facilitating assembling.

Also, as for the wiring method between the RF unit 23, antenna 95, and electroconductive membranes 96a and 96b, the other methods other than the method described in FIG. 15 are available, so any other method may be employed as long as it can connect a signal with a high-frequency.

Thus, with the capsule-type medical device 3F according to the fourth embodiment, in addition to the same advantages as the first embodiment, assembling can be readily performed without taking positioning of the antenna elements 95a and 95b into consideration, and the size of the antenna is set as close to the capsule size as possible, thereby improving antenna efficiency.

Note that the capsule-type medical device may be configured, as shown in FIG. 16 and FIG. 17, so as to enlarge the antenna size to make the length of the pair of the antenna elements 95a and 95b equal, or make the pair of the antenna elements 95a and 95b have a different shape.

As shown in FIG. 16, with a capsule-type medical device 3G, the two electroconductive membranes 96a and 96b making up the pair of antenna elements 95a and 95b are configured in a different shape. Further specifically, when facing the drawing, the electroconductive membrane 96b on the right side is formed extending up to a hemispheric-shaped portion end with respect to the electroconductive membrane 96a on the left side formed in a cylindrical shape having a transparent spherical portion where the image-capturing illumination unit 21 is disposed. Note that as for the lengths of the electroconductive membrane 96b on the right side and the electroconductive membrane 96a on the left side, these lengths are assumed to be the same value.

On the other hand, with a capsule-type medical device 3H shown in FIG. 17, in order to further enlarge the antenna size, the two electroconductive membranes 96a and 96b are each configured extending up to the capsule both ends. Further specifically, the two electroconductive membranes 96a and 96b are formed extending up to a hemispheric-shaped portion end.

Note that with the capsule-type medical devices 3F through 3H, the capsule frame body 11F may be formed with either a colored case or a transparent case if it is an application capsule for such as treatment or tissue sampling, other than image-capturing of an object.

On the other hand, with the capsule-type medical devices 3F through 3H, in the event of providing image-capturing unit, the capsule frame body 11F is formed with a transparent member, and also the electroconductive membranes 96a and 96b are formed with a transparent electroconductive member, e.g., amorphous transparent electroconductive film. Note that as for a low-resistance electroconductive membrane, insufficient InSb—ZnO family amorphous transparent electroconductive film and the like are available, but the other portions other than the portion where the image-capturing illumination unit is disposed may be covered with a membrane having high electroconductivity.

It is needless to say that these capsule-type medical devices 3G and 3H shown in FIG. 16 and FIG. 17 have the same configuration as the above fourth embodiment, and are subjected to wiring as to the RF unit 23, and include the respective built-in components other than this therein.

Thus, the capsule-type medical devices. 3G and 3H according to the present modification can improve antenna efficiency as compared with the above fourth embodiment by enlarging the antenna size as close to the capsule size as possible.

Note that embodiments or the like configured by partially combining the above embodiments are also encompassed in the present invention.

As described above, the capsule-type medical device according to the present invention has an advantage in that the efficiency of wireless transmission/reception using an antenna is improved, and radiowave power is increased.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule-type medical device comprising:
   a function executing unit for executing a predetermined function within a subject to be examined;
   a wireless unit for wirelessly sending a signal generated by the function executing unit being driven or for receiving a signal for controlling driving of the function executing unit; and
   an antenna having a pair of antenna elements in electrical connection with the wireless unit and formed in a tubular shape; wherein the antenna covers the outer circumference of the function executing unit.

2. The capsule-type medical device according to claim 1, wherein the function executing unit includes an illumination unit for illuminating the subject to be examined, and an image-capturing unit for taking in reflected light from the subject to be examined to form an image and capture this.

3. The capsule-type medical device according to claim 2, wherein the electrical connection between the wireless unit and the antenna passes through the inside of the pair of antenna elements.

4. The capsule-type medical device according to claim 2, wherein the antenna includes a slit portion in the direction of an axis in a tubular shape between the pair of antenna elements, and wherein the electrical connection between the wireless unit and the antenna is disposed in the slit portion.

5. The capsule-type medical device according to claim 2, wherein the pair of antenna elements are mutually disposed with an interval of equal to or more than one antenna element length therebetween.

6. The capsule-type medical device according to claim 2, wherein, the pair of antenna elements are configured with two electroconductive films formed on one board, and the one board is formed in a cylindrical shape; wherein the antenna elements surround at least one of the image-capturing unit, the illumination unit, and the wireless unit.

7. The capsule medical device according to claim 6, wherein the board is a flexible board.

8. The capsule medical device according to claim 2, further comprising a capsule frame body including the image-capturing unit, the illumination unit, and the wireless unit,
   wherein the pair of antenna elements are configured by forming two electroconductive membranes on an inner wall of the capsule frame body.

9. The capsule-type medical device according to claim 8, wherein the electrical connection between the two electroconductive membranes and the wireless unit is via two contact terminals having a spring function and being provided on the wireless unit.

10. The capsule medical device according to claim 8, wherein the two electroconductive membranes have a different shape.

11. The capsule-type medical device according to claim 1, wherein the electrical connection between the wireless unit and the antenna passes through the inside of the pair of antenna elements.

12. The capsule-type medical device according to claim 1, wherein the antenna includes a slit portion in the direction of an axis in a tubular shape between the pair of antenna elements, and wherein the electrical connection between the wireless unit and the antenna is disposed in the slit portion.

13. The capsule-type medical device according to claim 1, wherein the pair of antenna elements are mutually disposed with an interval of equal to or more than one antenna element length therebetween.

* * * * *